United States Patent
Grøndahl

(12) 
(10) Patent No.: US 6,281,013 B1
(45) Date of Patent: Aug. 28, 2001

(54) TREATMENT OF INFERTILITY

(75) Inventor: Christian Grøndahl, Vaerlose (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/528,917

(22) Filed: Mar. 20, 2000

Related U.S. Application Data

(63) Continuation of application No. PCT/DK00/00073, filed on Feb. 23, 2000.
(60) Provisional application No. 60/130,662, filed on Apr. 23, 1999.

(30) Foreign Application Priority Data

Feb. 24, 1999 (DK) ............................................. 1999 00256
Sep. 16, 1999 (DK) ............................................. 1999 01307

(51) Int. Cl.[7] ............................... C12N 5/00; C12N 5/02; C12N 5/06; C12N 15/68; C12N 5/10
(52) U.S. Cl. .......................... 435/363; 435/363; 435/325; 435/366; 514/21; 514/25; 424/184.1
(58) Field of Search ...................... 514/15, 2; 424/184.1, 424/185.1, 193.1, 19–22; 530/328, 402, 324; 435/69.1, 252.3, 320.1, 363

(56) References Cited

U.S. PATENT DOCUMENTS 4,845,077 * 4/1989 Hodgen ...................................... 514/2

FOREIGN PATENT DOCUMENTS

| WO 94/19455 | 9/1994 | (WO) . | |
|---|---|---|---|
| 96/00235 | * 1/1996 | (WO) | ............................... C07J/9/00 |
| WO 96/27658 | 9/1996 | (WO) . | |
| 97/000883 | * 1/1997 | (WO) | ............................... C07J/9/00 |
| WO 97/00884 | 1/1997 | (WO) . | |
| WO 98/28323 | 7/1998 | (WO) . | |
| WO 98/54965 | 12/1998 | (WO) . | |
| WO 98/55498 | 12/1998 | (WO) . | |

OTHER PUBLICATIONS

Ben–Nun et al., "Induction of artifical endometrial cycles with s. c. oestrogen implans and injectable progesterone in in–vitro fertilization treatment with donated oocytes: a preliminary report", Human Reproduction, Vo. 12 (10) pp. 2267–2270, 1997.*

Mar., Journal of Reproductive Medicine, vol. 38, No. 10, pp. 335–346 (1993).

Smitz et al., Human Reproduction, vol. 14, No. 1, pp. 145–161 (1999).

* cited by examiner

Primary Examiner—Karen Cochrane Carlson
Assistant Examiner—Patricia Robinson
(74) Attorney, Agent, or Firm—Reza Green, Esq.; Valeta A. Gregg, Esq.

(57) ABSTRACT

In an in vitro fertilization method, a woman is treated with a hypothalamic hormone and/or a pituitary hormone or an agonist or antagonist thereof or an active derivative thereof for a short period of time and, thereafter, using in vitro oocyte maturation egg or eggs are retrieved from the woman and are maturated using a meiosis activating compound.

21 Claims, No Drawings

TREATMENT OF INFERTILITY

CROSS-REFERENCE TO RELATED APPLICATIONS

This application is a continuation of PCT/DK00/00073 filed on Feb. 23, 2000 and claims priority under 35 U.S.C. 119 of Danish application no. PA 1999 00256 filed on Feb. 24, 1999, U.S. provisional application Ser. No. 60/130,662 filed on Apr. 23, 1999, and Danish application no. PA 1999 01307 filed on Sep. 16, 1999, the contents of which are fully incorporated herein by reference.

FIELD OF THIS INVENTION

This invention relates to an improved method of in vitro fertilisation (hereinafter designated IVF).

BACKGROUND OF THIS INVENTION

Since the first IVF pregnancy was delivered in 1978, this procedure has resulted in thousands of pregnancies and opened a vast new frontier of research and treatment for the infertile couples. Still, there is a significant need for improved infertility treatment modalities today. It is presumed that about one out of seven couples experience problems with subfertility or infertility.

IVF of human oocytes has become commonly used for the treatment of female and male subfertility. The standard IVF treatment includes a long phase of hormone stimulation of the female patient, e.g. 30 days, which is initiated by suppressing the patient's own follicle stimulating hormone (hereinafter designated FSH) and luteinising hormone (hereinafter designated LH) by gonadotropin releasing hormone (hereinafter designated GnRH), and this is followed by injections of exogenous gonadotropins, e.g. FSH and/or LH, in order to ensure development of multiple preovulatory follicles and aspiration of multiple in vivo matured oocytes immediately before ovulation. The aspirated oocyte is subsequently fertilised in vitro and cultured, typically for three days before transferral back into the uterus at the 4–8 cell stage. Continuous efforts have been made to optimise and simplify this procedure. Nevertheless, the overall pregnancy rate cannot be increased significantly over about 20% with the current treatment modalities. In a large European survey of IVF patients, it was found that 7.2 oocytes out of 11.5 aspirated oocytes per patient had undergone resumption of meiosis immediately before fertilisation, only 4.3 oocytes were fertilised and only 2.2 oocytes reached the 8-cell embryo stage after fertilisation and in vitro culture (ESHRE, Edinburgh, 1997).

Due to the very unpredictable quality of the state of the art embryos today, more than one embryo has to be transferred just to give a reasonable chance of success. Therefore, it is common to transfer 2–3 embryos (up to 5 embryos in some countries), which carries the very large side effect of multiple pregnancies with great discomfort and risk to both patient and children. Moreover, it has been estimated that the increased health care expenses due to multiple birth (twins, triplets etc.) is exceeding the entire IVF expenses.

Hence, there are several disadvantages with the current treatment, the four most notable being:

1. the risk of ovarian hyperstimulation with injecting gonadotropins which is a potential fatal condition that requires hospitalisation,
2. multiple pregnancies (50–1.000 times the normal frequency of twins and triplets, respectively),
3. the existence of considerable patient segments that do not tolerate the current method due to, e.g. polycystic ovarian syndrome and many diabetics, and
4. a potential long-term cancer risk.

Furthermore, weight gain, bloating, nausea, vomiting, labile mood and other patient discomforts together with patient reluctance to inject themselves are reported as disadvantages.

It is known from WO96/00235 that certain sterol derivatives can be used for regulating meiosis. An example of such a sterol is 4,4-dimethyl-5α-cholesta-8,14,24-triene-3β-ol (hereinafter designated FF-MAS).

Herein, the term MAS compounds designates compounds which mediate the meiosis of oocytes. More specifically, MAS compounds are compounds which in the test described in Example 1 below has a percentage germinal vesicle breakdown (hereinafter designated GVB) which is significantly higher than the control. Preferred MAS compounds are such having a percentage GVB of at least 50%, preferably at least 80%.

Examples of MAS compounds are mentioned in WO96/00235, 96/27658, 97/00884, 98/28323, 98/54965 and 98/55498, more specifically in claim 1 thereof.

In WO95/000265, some potential meiosis regulating substances were tested on immature female mice. 48 hours before the test animal were killed by cervical dislocation, they were given a single injection of human menopausal gonadotropin containing 20 IU FSH and 20 IU LH. The ovaries were removed, placed in a hypoxanthine medium and freed of extraneous tissue. Then, the oocytes were punctured out of the follicles, freed from cumulus cells and cultured in a medium containing a meiosis regulating derivative.

At present, in vitro maturation in humans has proven highly unsuccessful despite substantial interest and clinical efforts.

One object of the present invention is to treat human infertility.

Another object of the present invention is to improve the maturation of her human oocytes.

Another object of the present invention is to improve the synchrony of nuclear, cytoplasmic and/or membranous oocyte maturation.

Another object of the present invention is to improve the fertility of oocytes.

Another object of the present invention is to improve the rate of implantation of oocytes by human in vitro maturation and fertilisation.

Another object of the present invention is to diminish the incidence of human preembryos with chromosome abnormalities (aneuploidy).

Another object of the present invention is to improve the cleavage rate of human preembryos.

Another object of the present invention is to improve the quality of human preembryos.

SUMMARY OF THIS INVENTION

It has now, surprisingly, been found that the IVF treatment and the degree of side effects can be improved substantially if the woman, within a consecutive period of 30 days, avoids treatment with a hypothalamic hormone and/or a pituitary hormone or an agonist or antagonist thereof or an active derivative thereof (hereinafter this treatment is designated exogeneous stimulation) or if the exogeneous stimulation treatment of the female is only for a short period of time, e.g. less than 7 days, preferably less than 4 days. Using this improved method involving less or no exogeneous stimulation, a MAS compound is used to actively mature and synchronise human oocytes in vitro, leading to fertilisation and embryo development.

Briefly, the present invention relates to a method for human in vitro fertilisation wherein a woman, within a consecutive period of 30 days, is treated with a hypothalamic hormone and/or a pituitary hormone or an agonist or antagonist thereof or an active derivative thereof for a period which is less than about 7 days, preferably less than about 4 days, and, thereafter, using in vitro oocyte maturation wherein immature egg or eggs are retrieved from the woman and are in vitro matured in a synchronize manner using a MAS compound as defined herein. Preferred embodiments of this invention are those stated in the sub claims below.

DETAILED DESCRIPTION OF THIS INVENTION

Referring to the female cycle, one way of performing the IVF treatment of this invention is as follows:

Around days 6–9 in the cycle: Stimulation with FSH, e.g. 75–600 IU per day, preferably 150–225 IU per day, e.g. for 3 days.

Around day 9: The eggs are retrieved from the woman using ultrasound guided aspiration of small to medium size follicles with a diameter of about 6–12 mm, preferably 8–10 mm.

Around day 9–11: The eggs are maturated with a MAS compound in order to stimulate the meiosis. In this maturation step, the concentration of MAS compound may be in the range of about 0.1–100 $\mu$mol per litre, e.g. 10–20 $\mu$mol per litre. This medium may contain human serum albumin (hereinafter designated HSA), e.g. 0.8%, and it may additionally contain some ethanol, e.g., 0.4%, which has been used to dissolve MAS. The time for this maturation step may be in the range around 15–60 hours, e.g., about 22–40 hours, more specifically about 30–36 hours.

Around days 11–13: The eggs are fertilised in vitro.

Around days 12–16: The eggs are cultured in vitro in a suitable medium.

From the day before aspiration, the woman will receive an oestrogen, e.g. oestrogen valerate (2×10 mg daily). Two days later, she will also receive a progestogen, e.g., Progestane vagetoria, daily, which will render the lining of the uterus more prone to receive the future embryos. The duration of this treatment will be individually designed per patient. The doctor can chose among a variety of oestrogens and progestogens.

Around day 15–16: One or more embryos are transferred to the woman's uterus.

Hence, all in all, the complete treatment takes about 10–15 days.

Referring to the female cycle, another way of performing the IVF treatment of this invention is as follows:

Around days 2–8 in the cycle: Stimulation with FSH, e.g. 75–600 IU per day, preferably 150–225 IU per day, e.g. for 3 days, eventually spread over 6 days.

Around day 7–9: The eggs are retrieved from the woman using ultrasound guided aspiration of small to medium size follicles with a diameter of about 6–15 mm, preferably 8–12 mm.

Around day 7–11: The eggs are maturated with a MAS compound in order to stimulate the meiosis. In this maturation step, the concentration of MAS compound may be in the range of about 0.01–100 $\mu$mol per litre, e.g., 5–20 $\mu$mol per litre. This medium may contain human serum albumin (hereinafter designated HSA), e.g. 0.8%, and it may additionally contain some ethanol, e.g., 0.1–0.4%, which has been used to dissolve MAS. The time for this maturation step may be in the range around 15–60 hours, e.g., about 22–40 hours, more specifically about 30–36 hours.

Around days 9–13: The eggs are fertilised in vitro.

Around days 10–16: The eggs are cultured in vitro in a suitable medium.

From the day before aspiration, the woman will receive an oestrogen, e.g. oestrogen valerate (2×10 mg daily). Two days later, she will also receive a progestogen, e.g., Progestane vagetoria, daily, which will render the lining of the uterus more prone to receive the future embryos. The duration of this treatment will be individually designed per patient. The doctor can chose among a variety of oestrogens and progestogens.

Around day 13–16: One or more embryos are transferred to the woman's uterus.

Hence, all in all, the complete treatment takes about 10–15 days.

Most of the steps in the above treatment and procedure are performed in a known manner and the remaining steps are performed in a manner known per se. More details about the removal of the oocytes from follicles in the ovary, culturing of the isolated occytes, the culture medium to be used, the fertilisation with sperm, and the transfer of the embryo to the fallopian tube can be found in the literature, for example, in U.S. Pat. No. 5,693,534 which is hereby incorporated by reference.

According to this invention, the MAS compound is added to the culture me5 dium used. In this medium, the amount of the MAS compound is in the range from about 0.01 to about 100 $\mu$M, preferably in the range from about 0.1 to about 100 $\mu$M.

The reduced risk of side effects makes the method according to the present invention an attractive alternative to the current methods where GnRH is used for about 22 days and FSH is used for about 9 days before the eggs are retrieved and, thereafter, a progestogen is used for several weeks. Hence, using the treatment according to the present invention, the period in which the female patient is treated with a hypothalamic hormone and/or a pituitary hormone is reduced by about 80–90%. The total period of treatment by the current methods is about 4 weeks. Hence, using the treatment according to the present invention, the total period of treatment is reduced by about 50–60%.

Hypothalamic hormones are hormones present in the human hypothalamus. Pituitary hormones are hormones present in the human pituitary gland. Gonadotropic hormones are hormones secreted by the anterior lobe of the pituitary in vertebras and by mammalian placenta, which control the activity of gonads. Chemically, they are glycoproteins. Examples of gonadotropic hormones are FSH, LH and chorion gonadotropin, e.g. human chorion gonadotropin (hereinafter designated hCG). FSH stimulates growth of ovarian follicles and their oocytes in ovary and the formation of spermatozoa in testis. FSH can, e.g., be menopausal FSH or recombinant FSH. In females, LH activates the oestrogen-producing tissue of the ovaries to produce progesterone, probably promotes the final stages of the development of ovarian follicles, initiates the final oocyte maturation, induces ovulation and in mammals initiates corpus luteum development. These hormones are known. It is obvious for the skilled art worker that, alternatively, agonists or antagonists of these hormones can be used. It is also obvious for the skilled art worker that, alternatively, active analogues of these hormones can be used. Some of these agonists, antagonists and analogues are known and other can be prepared by process known per se. Examples of such known processes are chemical synthesis and genetic engineering.

In a preferred embodiment, the present invention relates to a method or use wherein the period in which said woman is treated with a hypothalamic hormone and/or a pituitary tuitary hormone or an agonist or antagonist thereof or an active derivative thereof is 0 (zero) days.

In a further preferred embodiment, the present invention relates to a method or use wherein the woman is treated for infertility, and/or for improving the maturation of her oocytes, and/or for improving the synchrony of nuclear, cytoplasmic and/or membranous oocyte maturation, and/or for improving the fertility of her oocytes, and/or for improving the rate of implantation of her oocytes by human in vitro maturation and fertilisation.

In a further preferred embodiment, the present invention relates to a method or use wherein the consecutive period is one menstrual cycle.

In a further preferred embodiment, the present invention relates to a method or use wherein the hormones are gonadotropic releasing hormones or an agonist or antagonist thereof or analogues thereof or gonadotropic hormones or an agonist or antagonist thereof or analogues thereof.

In a further preferred embodiment, the present invention relates to a method or use wherein the gonadotropic hormone is FSH or an agonist or antagonist thereof or analogues thereof.

In a further preferred embodiment, the present invention relates to a method or use wherein the period in which the female patient is treated with FSH or an agonist or antagonist thereof or analogues thereof, prior to the retrieval of the egg, is less than 7 days, preferably less than 4 days, and is at least 1 day.

In a further preferred embodiment, the present invention relates to a method or use wherein the period in which the female patient is treated with FSH or an agonist or antagonist thereof or analogues thereof is 2, 3 or 4 days.

In a further preferred embodiment, the present invention relates to a method or use wherein no chorion gonadotropin, e.g. human chorion gonadotropin or an agonist or antagonist thereof or analogues thereof is used.

In a further preferred embodiment, the present invention relates to a method or use wherein no gonadotropic releasing hormone, e.g. GnRH, or an agonist or antagonist thereof or analogues thereof is used.

In a further preferred embodiment, the present invention relates to a method or use wherein the dosage of MAS compound is in the range from about 0.01 $\mu$M per litre to about 100 $\mu$M per litre, preferably in the range from about 0.1 $\mu$M per litre to about 100 $\mu$M per litre.

In a further preferred embodiment, the present invention relates to a method or use wherein the MAS compound is one of the compounds mentioned in WO96/00235, 96/27658, 97/00884, 98/28323, 98/54965 and 98/55498, more specifically compounds mentioned in claim 1 thereof.

In a further preferred embodiment, the present invention relates to a method or use wherein the MAS compound is FF-MAS.

Additionally, the present invention relates to the use of a hypothalamic hormone and/or a pituitary hormone or an agonist or antagonist thereof or an active derivative thereof in the manufacture of a hormone product which is to be administered to a woman who, within a consecutive period of 30 days, is treated with a hypothalamic hormone and/or a pituitary hormone or an agonist or antagonist thereof or an active derivative thereof for a period which is less than about 7 days, preferably less than about 4 days, and from whom, immediately after said period, one or more oocytes are aspirated, where after said oocyte(s) is/are cultivated in a convenient medium containing a MAS compound as defined herein, where after said oocyte(s) is/are fertilised with human sperm, and, where after, the resulting embryo(s) is/are transferred to a woman.

Additionally, the present invention relates to use of a hypothalamic hormone and/or a pituitary hormone or an agonist or antagonist thereof or an active derivative thereof and of a MAS compound for the manufacture of a medicament for the treatment of human in vitro fertilisation wherein a hypothalamic hormone and/or a pituitary hormone or an agonist or antagonist thereof or an active derivative thereof is, within a consecutive period of 30 days, used to treat a women for a period which is less than about 7 days, preferably less than about 4 days, and, thereafter, the MAS compound is used in an in vitro oocyte maturation of the egg or eggs retrieved from this woman.

Additionally, the present invention relates to a pharmaceutically kit in unit dosage form for use by in vitro fertilisation comprising 1–8 separate unit dosages, said kit comprising less than 7, preferably less than 4, and at least 1 separate dosage units for sequential daily administration of a hypothalamic hormone and/or a pituitary hormone or an agonist or antagonist thereof or an active derivative thereof for sequential daily administration and 1 dosage units of a MAS compound. This kit may have the preferred features described above.

The present invention is further illustrated by the following examples, which, however, ever are not to be construed as limiting. The features disclosed in the foregoing description, scription,in the following examples and in the claims may, both separately and in any combination thereof, be material for realising the invention in diverse forms thereof.

EXAMPLE 1

Method used for electing MAS compounds Oocytes were obtained from immature female mice (C57 BL/6 J×DBA/2J F1, Bomholtgaard, Denmark) weighing 13–16 grams, that were kept under controlled temperature (20–22° C.), light (lights on 06.00–18.00) and relative humidity (50–70%). The mice received an intra-peritoneal injection of 0.2 ml gonadotropins (Gonal-F, Serono) containing 20 IU FSH and 48 hours later the animals were killed by cervical dislocation. The ovaries were dissected out and the oocytes were isolated in Hx-medium (see below) under a stereomicroscope by manual rupture of the follicles using a pair of 27 gauge needles. Spherical oocytes displaying an intact germinal vesicle (hereinafter designated GV) were divided in cumulus enclosed oocytes (hereinafter designated CEO) and naked oocytes (hereinafter designated NO) and placed in $\alpha$-minimum essential medium ($\alpha$-MEM without ribonucleosides, Gibco BRL, Cat. No. 22561) supplemented with 3 mg/ml bovine serum albumin (BSA, Sigma Cat. No. A7030), 5 mg/ml human serum albumin (HSA, Statens Seruminstitut, Denmark), 0.23 mM pyruvate (Sigma, Cat. No S-8636), 2 mM glutamine (Flow Cat. No.16–801), 100 IU/ml penicillin and 100 $\mu$g/ml streptomycin (Flow, Cat No.16–700). This medium was supplemented with 3 mM hypoxanthine (Sigma Cat. No. H-9377) and designated Hx-medium. The oocytes were rinsed three times in Hx-medium and oocytes of uniform size were divided into groups of CEO and NO. CEO and NO were cultured in 4-well multidishes (Nunclon, Denmark) in which each well contained 0.4 ml of Hx-medium and the compound to be tested in a concentration of 10 $\mu$M. One control well (i.e., 35–45 oocytes cultured in identical medium with no addition of test compound) was always cultured simultaneously with 3 test wells (35–45 oocytes per well supplemented with test compound). The oocytes were cultured in a humidified atmosphere of 5% $CO_2$ in air for 24 hours at 37° C. By the end of the culture period, the number of oocytes with GV, GVB and polar bodies (hereinafter designated PB), respectively, were counted using a stereo microscope (Wildt, Leica MZ 12). The percentage of GVB, defined as percentage of oocytes undergoing GVB per total number of oocytes in that well, was calculated as: % GVB=((number of GVB+ number of PB)/total number of oocytes)×100.

EXAMPLE 2

Patients for in vitro fertilisation (IVF) normally undergo a long (4 weeks) gonadotropin based protocol that leads to the aspiration of in vivo matured oocytes. These oocytes are subsequently fertilised in vitro and replaced as 4–8 cell embryos to the uterus of the patient by a cervical catheter. In vitro maturation with FF-MAS Procedure All IVF patients can potentially receive this treatment, age range 20 to 45 year with or without displaying Polycystic ovarian syndrome (PCO) and with or without a regular cycle. In the case of irregular cycle or amemorhea (no cyclic activity) this procedure could be preceded with oral contraceptive for various lengths (1–10 month) and with drawn upon initiation of the following procedure. In the beginning (day 1–6, preferably day 3–6) of the cycle (day $1=1^{st}$ day of menses), the patient will be clinically examined and may or may not receive a small priming FSH stimulus individually designed for each patient (length: 1–7 days, doses: 75 IU to 750 IU, preferentially 3–4 days with doses 150 to 300 IU recombinant or urinary based FSH) with or without the use of GNRH antagonist and with or without hCG. Small to medium size follicles (size: 4 to 16 mm, preferential 8 to 12 mm follicles) will be aspirated under ultrasound guidance using a low/reduced suction pressure and specially designed (more rigid) needles. The aspirated fluid will be searched for cumulus oocytes complexes (COC) and once identified under the stereomicroscope (with or without the use of embryo filters), the COC will be placed in culture. A wide variety of oocyte culture media or media components known to the skilled worker can be used, however the oocytes will be induced to resume meiotic maturation by exposure to FF-MAS. Human serum albumin (HSA) may or may not be added to the medium. If added, it can be in a concentration of 0.1 to 100 mg/ml, preferentially 5 to 15 mg/ml or 0.5 to 1.5% (volume/volume. The formulation of FF-MAS may be in the form of an ethanol stock solution, DMSO or other organic solvent solution or it may be in form of FF-MAS/HSA dry coated wells ready to use just by adding the appropriate culture medium. The duration of in vitro maturation may vary from 4 to 60 hours, preferentially 30 to 40 hours. The concentration of FF-MAS may vary from 0.01 $\mu$M to 100 $\mu$M preferably from 0.1 $\mu$M to 100 $\mu$M, more preferred from 5 $\mu$M to 30 $\mu$M, even more preferred from 10 $\mu$M to 30 $\mu$M. Following in vitro maturation, the oocytes may be fertilised by conventional IVF or by intracytoplasmatic sperm injection (hereinafter designated ICSI) or by future appropriate fertilisation methods leading to fertilised zygotes and the developing embryo may be transferred on day 1 to day 6 after fertilisation, preferentially on day 2 to 3, either as single egg transfer or multiple egg transfer. The patient can receive progesterone and/or oestrogen therapy before and after the transfer in individually designed protocols to prime and sustain appropriate receptive endometrial lineage.

Compared with the know procedures, better results were obtained using the above procedure.

EXAMPLE 3

Use of FF-MAS for in vitro maturation of immature human oocytes

The female patient was started on a brief ovarian stimulation with recombinant FSH with an average daily dose of 225 on day 2 in the cycle and continued for a total of three times on alternating days, i.e., $2^{nd}$, $4^{th}$, and $6^{th}$ day in the cycle. At least 3 follicles of 10 mm or more on day 7 lead to aspiration of immature follicles in the size between 8–12 mm. Follicles were aspirated and immature (GV stage) cumulus enclosed oocytes were cultured in oocyte culture system containing a standard in vitro culture (IVC) media (IVF 20 (which is available from Scandinavian IVF Science AB, Gothenburg, Sweden)) additionally containing human serum albumin (0.8%) and FF-MAS (5 $\mu$M). All oocytes were cultured under normal conditions at 37° C. in the incubator. Each oocyte was cultured in one well in a four-chamber culture dish as culture media system. The duration of exposure to the culture media with treatment was 30 hours before ICSI or in vitro fertilization was performed. Preembryos were evaluated for cleavage stage and fragmentation / morphology at 1, 2 and 3 days post ICSI/IVF. After 3 days of culture, a selection of the best preembryos, typically two preembryos, were replaced to the female patient.

Compared with the know procedures, similar clinical outcome was obtained. However, in this example, compared with the known procedures, a reduced hormone exposure was used and, consequently, a reduced side effect profile was obtained here.

EXAMPLE 4

Using the procedure described in Example 3 with the proviso that in stead of using FF-MAS in a concentration of 5 $\mu$M, FF-MAS was used in a concentration of 20 $\mu$M, similar clinical outcome was obtained in this procedure as was obtained with the known procedures. However, in this example, compared with the known procedures, a reduced hormone exposure was used and, consequently, a reduced side effect profile was obtained here.

What is claimed is:

1. A method for in vitro fertilization of human oocytes, comprising:
    (a) treating a female patient, within one consecutive period, with hypothalamic or pituitary hormone, or an agonist or analogue thereof, for a period of less than 7 days;
    (b) retrieving an oocyte(s) from the patient after the less than 7 day treatment period;
    (c) exposing the oocyte(s) to a meiosis activating substance (MAS), wherein in vitro oocyte maturation is achieved; and
    (d) fertilizing the in vitro matured oocyte(s).
2. The method of claim 1, wherein the treatment of step (a) is less than 4 days.
3. The method of claim 1, wherein the consecutive period is one menstrual cycle.
4. The method of claim 1, wherein the hypothalamic hormone is (i) gonadotropic releasing hormones, an agonist, antagonist, or analogue thereof, or (ii) gonadotropic hormones having follicle stimulating hormone (FSH) or leutinizing hormone (LH) activity, or an agonist, antagonist, or analogue thereof.

5. The method of claim 4, wherein the gonadotropic hormone is FSH.

6. The method of claim 4, wherein the gonadotropic hormone is LH.

7. The method of claim 4, wherein the gonadotropic hormone is human chorion gonadotropin (hCG).

8. The method of claim 5, wherein patient is treated in step (a) with FSH, an agonist, antagonist, or analogue thereof, and the treatment period is less than 7 days and at least 1 day.

9. The method of claim 6, wherein patient is treated in step (a) with FSH, an agonist, antagonist, or analogue thereof, and the treatment period is less than 7 days and at least 1 day.

10. The method of claim 8, wherein the treatment period is 2, 3, or 4 days.

11. The method of claim 1, wherein no chorion gonadotropin, an agonist, antagonist, or analogue thereof, is used.

12. The method of claim 11, wherein no gonadotropin releasing hormone, an agonist, antagonist, or analogue thereof, is used.

13. The method of claim 1, wherein the MAS compound is present in the range of 0.1 to 100 $\mu$M.

14. A method according to claim 1, wherein the MAS compound is one of the compounds mentioned in WO96/00235, 96/27658, 97/00884, 98/28323, 98/54965 and 98/55498.

15. A pharmaceutically kit for use in in vitro fertilization, comprising
   (i) 1–8 separate unit dosages for sequential daily administration of a hypothalamic hormone, an agonist, antagonist, or analogue thereof, and/or a pituitary hormone, an agonist, antagonist, or analogue thereof, and
   (ii) 1 dosage units of a MAS compound.

16. The kit of claim 15, comprising less than 4 separate dosage units of a hypothalamic hormone, an agonist, antagonist, or analogue thereof, and/or a pituitary hormone, an agonist, antagonist, or analogue thereof.

17. A method for in vitro fertilization of human oocytes, comprising:

(a) treating a female patient, within one consecutive period, with follicle stimulating hormone (FSH), or an agonist or analogue thereof, in the absence of chorion gonadotropin and/or gonadotropin releasing hormone, for a period of less than 4 days;

(b) retrieving an oocyte(s) from the patient after the less than 4 day treatment period;

(c) exposing the oocyte(s) to a meiosis activating substance (MAS), wherein in vitro oocyte maturation is achieved; and (d) fertilizing the in vitro matured oocyte(s).

18. The method of claim 17, wherein the consecutive period is one menstrual cycle.

19. The method of claim 17, wherein the treatment period is 1, 2, or 3 days.

20. The method of claim 17, wherein the MAS compound is present in the range of 0.1 to 100$\mu$M.

21. The method of claim 17, wherein the MAS compound is FF-MAS.

* * * * *